(12) United States Patent
Mei (10) Patent No.: US 12,364,093 B2
(45) Date of Patent: Jul. 15, 2025

(54) LUMINESCENT DEVICE, MANUFACTURING METHOD THEREOF, AND DISPLAY APPARATUS

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Wenhai Mei, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 17/770,501

(22) PCT Filed: May 31, 2021

(86) PCT No.: PCT/CN2021/097374
§ 371 (c)(1),
(2) Date: Apr. 20, 2022

(87) PCT Pub. No.: WO2022/252049
PCT Pub. Date: Dec. 8, 2022

(65) Prior Publication Data
US 2024/0164126 A1 May 16, 2024

(51) Int. Cl.
*H01L 51/50* (2006.01)
*H10K 50/115* (2023.01)
*H10K 50/16* (2023.01)

(52) U.S. Cl.
CPC .......... *H10K 50/115* (2023.02); *H10K 50/16* (2023.02)

(58) Field of Classification Search
None
See application file for complete search history.

(56) References Cited

FOREIGN PATENT DOCUMENTS

CN 111384273 A * 7/2020 ............. H10K 51/50

* cited by examiner

*Primary Examiner* — Gregory D Clark
(74) *Attorney, Agent, or Firm* — WHDA, LLP (57) ABSTRACT

A luminescent device, a manufacturing method thereof, and a display apparatus, the luminescent device may avoid a fluorescence quenching problem of the quantum dot light-emitting layer due to the influence of the electron transport layer. The luminescent device includes: an anode, a quantum dot light-emitting layer, an electron transport layer, and a cathode in a stacked arrangement; the electron transport layer includes inorganic oxide nanoparticles and a porous frame structure, and the inorganic oxide nanoparticles are anchored in pores of the porous frame structure; the porous frame structure is configured to be formed by ligand reaction; a general structural formula of the ligand includes: A-X-Q; A is a coordinating group, and is configured to coordinate with the inorganic oxide nanoparticles, X is a regulator group, and is configured to increase or decrease an electron mobility, and Q is a frame group, and is configured to form a frame structure.

20 Claims, 1 Drawing Sheet

LUMINESCENT DEVICE, MANUFACTURING METHOD THEREOF, AND DISPLAY APPARATUS

TECHNICAL FIELD

The present disclosure relates to the technical field of display, and more particularly, to a luminescent device, a manufacturing method thereof, and a display apparatus.

BACKGROUND

A quantum dots light emitting diode display (QLED) device with fluorescent quantum dots as a luminescent layer is a kind of display and luminescent device with great potential. Currently, quantum dots are used as the light-emitting layer, organic compounds are used as the hole transport layer, and inorganic metal oxide nanoparticles (such as zinc oxide nanoparticles) are used as the electron transport layer to form a hybrid 'sandwich structure', thereby forming an effective QLED device. The device performance of the QLED device with cadmium-containing quantum dots as the light-emitting layer has reached the current development level of organic light-emitting diode devices.

However, in the QLED device, the electron transport layer may affect the quantum dot light-emitting layer, resulting in the fluorescence quenching of the quantum dots, reducing the light-emitting efficiency, and ultimately affecting the performance of the device.

SUMMARY

The embodiments of the present disclosure provide a luminescent device, a manufacturing method thereof, and a display apparatus, the luminescent device may avoid a fluorescence quenching problem of the quantum dot light-emitting layer due to the influence of the electron transport layer, thereby improving the light-emitting efficiency and improving the device performance.

In order to achieve the above purpose, the embodiments of the present disclosure use the following technical solutions:

in one aspect, a luminescent device is provided, and the luminescent device includes: an anode, a quantum dot light-emitting layer, an electron transport layer, and a cathode in a stacked arrangement;

the electron transport layer includes inorganic oxide nanoparticles and a porous frame structure, and the inorganic oxide nanoparticles are anchored in pores of the porous frame structure;

the porous frame structure is configured to be formed by ligand reaction; a general structural formula of the ligand comprises: A-X-Q;

wherein, A is a coordinating group, and is configured to coordinate with the inorganic oxide nanoparticles, X is a regulator group, and is configured to increase or decrease an electron mobility, and Q is a frame group, and is configured to form a frame structure.

Optionally, A includes any one of an amino,

Optionally, X includes any one of a triphenylamine unit, a carbazole unit, and a pyridine unit.

Optionally, Q includes any one of a first group unit, a hydroxyl group, and a cyanide group; wherein the first group unit includes a first group and a second group, the first group includes a boronic acid group, and the second group includes halogen.

Optionally, the ligand includes any one of:

Optionally, when the ligand includes the porous frame structure includes wherein R represents

Optionally, when the ligand includes the porous frame structure includes

Optionally, when the ligand includes the porous frame structure includes

Optionally, the inorganic oxide nanoparticles includes any one of zinc oxide nanoparticles, zirconia nanoparticles, aluminum oxide nanoparticles, magnesium zinc oxide nanoparticles, magnesium oxide nanoparticles, and titanium dioxide nanoparticles.

Optionally, the luminescent device is inverted, and a material of the cathode includes indium tin oxide.

In another aspect, a display apparatus is provided, and the display apparatus includes the above-mentioned luminescent device.

In another aspect, a manufacturing method of the above-mentioned luminescent device is provided, and the method includes:

forming the anode, the quantum dot light-emitting layer, the electron transport layer, and the cathode in the stacked arrangement on a substrate; wherein the electron transport layer includes the inorganic oxide nanoparticles and the porous frame structure, the inorganic oxide nanoparticles are anchored in the pores of the porous frame structure; the porous frame structure is configured to be formed by reacting with the ligand; the general structural formula of the ligand comprises: A-X-Q; A is the coordinating group, and is configured to coordinate with the inorganic oxide nanoparticles, X is the regulator group, and is configured to increase or decrease the electron mobility, and Q is the frame group, and is configured to form the frame structure.

Optionally, forming the electron transport layer includes:

forming an inorganic-oxide-nanoparticle material and a ligand material;

mixing the inorganic-oxide-nanoparticle material and the ligand material, to form a precursor material;

coating the precursor material on the substrate; and performing a microwave reaction to the substrate formed with the precursor material, to obtain the electron transport layer.

Optionally, performing the microwave reaction to the substrate formed with the precursor material includes:

placing the substrate formed with the precursor material in a microwave generator, and performing the microwave reaction at a preset temperature for a preset time.

Optionally, a range of the preset temperature is 50° C.-200° C., and the preset time is 5 minutes to 60 minutes.

Optionally, forming the anode, the quantum dot light-emitting layer, the electron transport layer, and the cathode in the stacked arrangement on the substrate includes:

sequentially forming the cathode, the electron transport layer, the quantum dot light-emitting layer, and the anode in the stacked arrangement.

The above description is merely a summary of the technical solutions of the present disclosure. In order to more clearly know the elements of the present disclosure to enable the implementation according to the contents of the description, and in order to make the above and other purposes, features, and advantages of the present disclosure more apparent and understandable, the particular embodiments of the present disclosure are provided below.

BRIEF DESCRIPTION OF THE DRAWINGS

In order to more clearly illustrate the technical solutions of the embodiments of the present disclosure or the prior art, the figures that are required to describe the embodiments or the prior art will be briefly introduced below. Apparently, the figures that are described below are embodiments of the present disclosure, and a person skilled in the art may obtain other figures according to these figures without paying creative work.

DETAILED DESCRIPTION OF THE EMBODIMENTS

In order to make the objects, the technical solutions, and the advantages of the embodiments of the present disclosure clearer, the embodiments of the present disclosure will be clearly and completely described below with reference to the drawings of the embodiments of the present disclosure. Apparently, the described embodiments are merely certain embodiments of the present disclosure, rather than all of the embodiments. All of the other embodiments that a person skilled in the art obtains on the basis of the embodiments of the present disclosure without paying creative work fall within the protection scope of the present disclosure.

In the embodiments of the present disclosure, words such as "first" and "second" are used to distinguish the same items or similar items with basically the same functions and effects, which are only for the purpose of clearly describing the technical solutions of the embodiments of the present disclosure, and should not be understood to indicate or imply relative importance or to imply the quantity of technical features indicated. In addition, "plurality" means two or more, and "at least one" means one or more, unless expressly defined otherwise.

In the related art, when an inorganic metal oxide is used as an electron transport layer, it may affect the quantum dot light-emitting layer. Taking zinc oxide as an example to illustrate, defective sites on the surface of zinc oxide, such as hydroxyl functional groups (—OH) and oxygen vacancies may lead to rapid degradation of the device, therefore, resulting in a roll-off phenomenon of the device efficiency. At the same time, hydroxyl and oxygen vacancies on the surface of the hydrophilic zinc oxide film may destroy the surface ligand of the fluorescent quantum dots, and resulting in a fluorescence quenching of the quantum dots, thereby reducing the life of the device and limiting the improvement of the device performance. In addition, in different device structures, the zinc oxide electron film layer may cause the unbalanced injection of holes and electrons in the device, which greatly limits the performance of the QLED devices.

Figure 1:
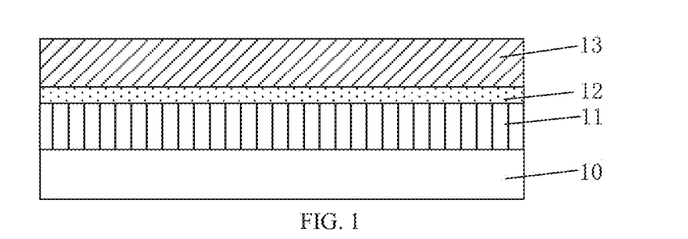
FIG. 1 schematically illustrates a structural schematic diagram of a luminescent device.
Figure 2:
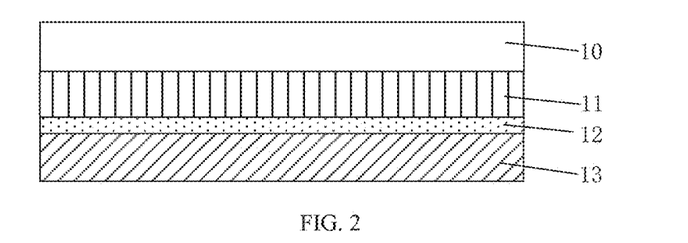
FIG. 2 schematically illustrates a structural schematic diagram of another luminescent device.

Based on the above, an embodiment of the present disclosure provides a luminescent device, as shown in FIG. 1 and FIG. 2, the luminescent device includes: an anode 10, a quantum dot light-emitting layer 11, an electron transport layer 12, and a cathode 13 in a stacked arrangement.

Figure 3:
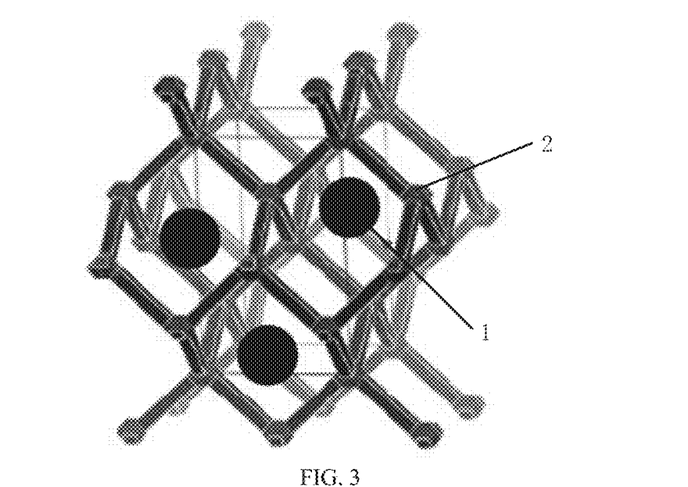
FIG. 3 schematically illustrates a structural schematic diagram of an electron transport layer.

Referring to FIG. 3, the electron transport layer includes inorganic oxide nanoparticles 1 and a porous frame structure 2, and the inorganic oxide nanoparticles 1 are anchored in pores of the porous frame structure 2.

The porous frame structure is configured to be formed by a ligand reaction; a general structural formula of the ligand includes: A-X-Q; wherein, A is a coordinating group, and is configured to coordinate with the inorganic oxide nanoparticles, X is a regulator group, and is configured to increase or decrease an electron mobility, and Q is a frame group, and is configured to form a frame structure.

The specific structure of the above-mentioned porous frame structure is not limited, and it may be obtained by reacting with the ligand. The above-mentioned ligand may form the porous frame structure by a microwave reaction, certainly, it may also be obtained by other reactions, which is not limited here.

The specific materials of the above-mentioned inorganic oxide nanoparticles are not limited. For example, the inorganic oxide nanoparticles may include inorganic metal oxide nanoparticles, such as zinc oxide nanoparticles or zirconia nanoparticles, and so on. Certainly, other types may also be included.

The above-mentioned quantum dot light-emitting layer may include quantum dots, and the quantum dots may include a core-shell structure or a perovskite nanocrystal structure. Specifically, the core-shell structure may include an inner core layer and a cladding layer surrounding the inner core layer, the material of the inner core layer may be cadmium selenide (CdSe) or cadmium sulfide (CdS), and the material of the cladding layer is any one of zinc sulfide (ZnS), zinc oxide (ZnO) and zinc selenide (ZnSe). The core-shell structure in which cadmium selenide forms the inner core layer and zinc sulfide forms the cladding layer is often used to form quantum dots. In order to realize colorized display, the quantum dot light-emitting layer may include red quantum dots, green quantum dots and blue quantum dots. Certainly, the quantum dot light-emitting layer may also include only one of the red quantum dots, the green quantum dots, and the blue quantum dots, to realize the display of a single color.

According to different manufacturing sequences, the above-mentioned luminescent device may be divided into the upright luminescent device shown in FIG. 1 and the inverted luminescent device shown in FIG. 2. Specifically, as shown in FIG. 1, the manufacturing sequence of the upright luminescent device is to form the anode 10, the quantum dot light-emitting layer 11, the electron transport layer 12 and the cathode 13 in sequence. Referring to FIG. 2, the manufacturing sequence of the inverted luminescent device is to form the cathode 13, the electron transport layer 12, the quantum dot light-emitting layer 11 and the anode 10 in sequence.

The inventor found through research that, in the manufacturing process of the inverted luminescent device, when the electron transport layer is directly coated on the cathode, and the electron transport layer is directly contact with the cathode, the finally formed luminescent device is prone to have problems of poor appearance after lighting, and some area not glowing. In the inverted luminescent device provided by the present disclosure, the inorganic oxide nanoparticles may be anchored in the pores of the porous frame structure via coordination, to avoid the direct contact between the inorganic oxide nanoparticles and the cathode, thereby improving the appearance of the inverted luminescent device, and improving the device performance.

In the luminescent device provided in the present disclosure, the electron transport layer includes the inorganic oxide nanoparticles and the porous frame structure, and the inorganic oxide nanoparticles may be anchored in the pores of the porous frame structure via coordination, which may avoid that the inorganic oxide nanoparticles and the quantum dot light-emitting layer are in direct contact, to avoid the quenching of the luminescence of the quantum dots by oxygen vacancies and groups on the surface of the inorganic oxide nanoparticles, thereby improving the luminescence efficiency and improving the device performance. In addition, the porous frame structure of the electron transport layer is formed by the ligand including the regulator group X, and the regulator group X may increase or decrease the electron mobility, that is, the electron mobility of the electron transport layer may be adjusted by the regulator group X, thereby improving the problem of the unbalanced injection of the holes and the electrons in the luminescent device, and greatly improves the device performance.

Optionally, in order to improve the coordination ability, A includes any one of an amino, to better embed the inorganic oxide nanoparticles in the pores of the porous frame structure.

Optionally, in order to improve the problem of the unbalanced injection of the holes and the electrons, X includes any one of a triphenylamine unit, a carbazole unit, and a pyridine unit. Wherein, the triphenylamine unit and the carbazole unit are beneficial to hole transport, that is, may reduce the electron mobility; the pyridine unit is beneficial to electron transport, that is, the electron mobility may be increased. The triphenylamine unit includes group, the carbazole unit includes group, and the pyridine unit includes group.

Optionally, in order to facilitate the realization of the frame structure, Q includes any one of a first group unit, a hydroxyl group, and a cyanide group; wherein the first group unit includes a first group and a second group, the first group includes a boronic acid group, and the second group includes halogen. For example, Q between adjacent ligands may be bonded together to form the porous frame structure.

It should be noted that boronic acid group may include

The first group may also include which is not limited here. The halogen may include chlorine (CL), bromine (Br), iodine (I), and so on.

Optionally, in order to facilitate the realization, the ligand includes any one of:

NH2, and

In one or more embodiments, when the ligand includes the porous frame structure includes wherein R represents

The chemical formula for the ligand to form the porous framework structure is as follows:

that is the ligand may be microwaved at 100° C. for 60 min to form a porous framework structures including It should be noted that the amino in the framework unit of the porous frame structure has a strong coordination effect on the inorganic oxide nanoparticles, so that the inorganic oxide nanoparticles are disposed in the pores of the porous frame structure.

In one or more embodiments, when the ligand includes and Br between adjacent ligands may react, to form a porous framework structures including In one or more embodiments, when the ligand includes OH between adjacent ligands may react, to form a porous framework structures including Optionally, the inorganic oxide nanoparticles include any one of zinc oxide nanoparticles, zirconia nanoparticles, aluminum oxide nanoparticles, magnesium zinc oxide nanoparticles, magnesium oxide nanoparticles, and titanium dioxide nanoparticles. Wherein the zinc oxide nanoparticles are more widely used.

Optionally, the above-mentioned luminescent device is inverted, and a material of the cathode includes indium tin oxide (ITO). The inverted luminescent device provided by the present disclosure may avoid the direct contact between the inorganic oxide nanoparticles and the indium tin oxide, thereby improving the appearance of the inverted luminescent device, and improving the device performance.

Certainly, the material of the cathode may also include other materials, such as silver, and so on.

Figure 4:
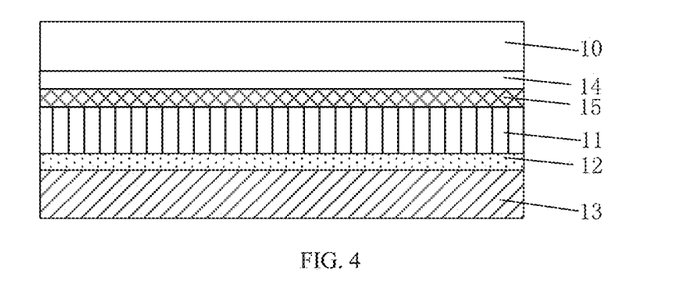
FIG. 4 schematically illustrates a structural schematic diagram of another luminescent device.

It should be noted that, as shown in FIG. 4, the luminescent device may further include a hole injection layer 14 and a hole transport layer 15 located between the anode 10 and the quantum dot light-emitting layer 11, wherein the hole injection layer 14 is closer to the anode 10 compared with the hole transport layer 15.

An embodiment of the present disclosure further provides a display apparatus, including: the above-mentioned luminescent device.

The display apparatus may be a QLED display apparatus, and may also be any product or component including the QLED display apparatus with a display function, such as a TV, a digital camera, a mobile phone, a tablet computer, etc.; which has the advantages of high light output efficiency, no cross color, high resolution, and good display performance.

An embodiment of the present disclosure further provides a manufacturing method of the above-mentioned luminescent device, and the method includes:

S01, forming the anode, the quantum dot light-emitting layer, the electron transport layer, and the cathode in the stacked arrangement on a substrate; wherein the electron transport layer comprises the inorganic oxide nanoparticles and the porous frame structure, the inorganic oxide nanoparticles are anchored in the pores of the porous frame structure; the porous frame structure is configured to be formed by reacting with the ligand; the general structural formula of the ligand comprises: A-X-Q; A is the coordinating group, and is configured to coordinate with the inorganic oxide nanoparticles, X is the regulator group, and is configured to increase or decrease the electron mobility, and Q is the frame group, and is configured to form the frame structure.

It should be noted that, the above step S01 may include: sequentially forming the anode, the quantum dot light-emitting layer, the electron transport layer, and the cathode in the stacked arrangement, to form an upright luminescent device; or may also include: sequentially forming the cathode, the electron transport layer, the quantum dot light-emitting layer, and the anode in the stacked arrangement, to form an inverted luminescent device. Which is not limited here, and may select according to actual requirements.

For the description of the structure and material of each film layer in the luminescent device involved in the above manufacturing method, reference may be made to the foregoing embodiments of the luminescent device, which will not be repeated here.

In the luminescent device formed by performing step S01, the electron transport layer includes the inorganic oxide nanoparticles and the porous frame structure. The inorganic oxide nanoparticles may be anchored in the pores of the porous frame structure via coordination, which may avoid that the inorganic oxide nanoparticles and the quantum dot light-emitting layer are in direct contact, to avoid the quenching of quantum dot luminescence caused by oxygen vacancies and groups on the surface of the inorganic oxide nanoparticles, thereby improving the luminescence efficiency and the device performance. In addition, the porous frame structure of the electron transport layer is formed by the ligand including the regulator group X, and the regulator group X may increase or decrease the electron mobility, that is, the electron mobility of the electron transport layer may be adjusted by the regulator group X, thereby improving the problem of the unbalanced injection of the holes and the electrons in the luminescent device, and greatly improving the device performance.

Optionally, the above forming the electron transport layer includes:

S101, forming an inorganic-oxide-nanoparticle material and a ligand material.

The specific formation methods of the inorganic-oxide-nanoparticle material and the ligand material are not limited here, and may be determined according to the specific material.

S102, mixing the inorganic-oxide-nanoparticle material and the ligand material, to form a precursor material.

S103, coating the precursor material on the substrate.

Specifically, the precursor material may be spin-coated on the substrate by a spin-coating method. If an upright luminescent device is formed, before spin-coating the precursor material on the substrate, an anode and a quantum dot light-emitting layer may be formed on the substrate in sequence; then, the precursor material may be spin-coated on the quantum dot light-emitting layer. If an inverted luminescent device is formed, before spin-coating the precursor material on the substrate, a cathode may also be formed on the substrate; then, the precursor material may be spin-coated on the cathode.

S104, performing a microwave reaction to the substrate formed with the precursor material, to obtain the electron transport layer.

The time and temperature of the microwave reaction are not limited here.

By performing S101-S104, the electron transport layer with the porous frame structure may be formed, and the inorganic oxide nanoparticles may be anchored in the pores of the porous frame structure via coordination. This method is simple and easy to implement.

Further optionally, S104, performing the microwave reaction to the substrate formed with the precursor material includes:

S104', placing the substrate formed with the precursor material in a microwave generator, and performing the microwave reaction at a preset temperature for a preset time.

Optionally, the range of the preset temperature is 50° C.-200° C., and the preset time is 5 minutes to 60 minutes. The specific temperature and time may be selected according to the precursor material. For example, the preset temperature may be 50° C., 70° C., 90° C., 100° C., 120° C., 150° C., 180° C. or 200° C. The preset time may be 10 minutes, 20 minutes, 30 minutes, 40 minutes, 50 minutes, or 60 minutes.

Optionally, the above step S01, forming the anode, the quantum dot light-emitting layer, the electron transport layer, and the cathode in the stacked arrangement on the substrate includes:

S01', sequentially forming the cathode, the electron transport layer, the quantum dot light-emitting layer, and the anode in the stacked arrangement, to form an inverted luminescent device.

For easy of description, are labeled as a ligand A, a ligand B, and a ligand C, respectively. The specific manufacturing process of the electron transport layer is described below by taking the ligand A, the ligand B and the ligand C as examples respectively.

In one or more embodiments, the porous frame structure of the electron transport layer is formed by the ligand A, and the inorganic oxide nanoparticles include zinc oxide nanoparticles.

The manufacturing method of the electron transport layer includes:

S21, forming zinc oxide nanoparticles.

For example, 0.22 g of zinc acetate is dissolved in 10 mL of DMSO (dimethyl sulfoxide); 0.33 g of tetramethylammonium hydroxide is dissolved in 3.3 mL of ethanol, and then dropped into the zinc acetate solution to react for 20 hours. Precipitation begins after adding about 1 times of ethyl acetate, and continue to add the ethyl acetate until the precipitation does not increase after adding about 1.5 times of the ethyl acetate. Centrifuge at 4200 rpm for 5 minutes at 20 degrees Celsius. Then the supernatant is poured off, 10 ml of the ethanol is added, and a zinc oxide ethanol solution is formed by dissolving via ultrasonication for 30 s or shaking for 30 s.

S22, adding 300 ul of a xylene/dioxane mixed solution (20 mg/ml) of the ligand A to the zinc oxide ethanol solution, and stirring for half an hour. Then, about 1-1.5 times of the ethyl acetate is added, after it is precipitated and the supernatant is removed by centrifugation, it may be dissolved in 8 mL of the ethanol to obtain a precursor solution.

S23, spin-coating the precursor solution obtained by S22 at a speed of 2000 rpm, placing the substrate in a microwave generator after the spin-coating is completed, and performing a microwave reaction at 100 degrees for 15 minutes, to form an electron transport layer with a porous frame structure.

In one or more embodiments, the porous frame structure of the electron transport layer is formed by the ligand B, and the inorganic oxide nanoparticles include zinc oxide nanoparticles.

The manufacturing method of the electron transport layer includes:

S31, forming zinc oxide nanoparticles.

For example, 0.22 g of zinc acetate is dissolved in 10 mL of DMSO (dimethyl sulfoxide); 0.33 g of tetramethylammonium hydroxide is dissolved in 3.3 mL of ethanol, and then dropped into the zinc acetate solution to react for 20 hours. Precipitation begins after adding about 1 times of ethyl acetate, and continue to add the ethyl acetate until the precipitation does not increase after adding about 1.5 times of the ethyl acetate. Centrifuge at 4200 rpm for 5 minutes at 20 degrees Celsius. Then the supernatant is poured off, 10 ml of the ethanol is added, and a zinc oxide ethanol solution is formed by dissolving via ultrasonication for 30 s or shaking for 30 s.

S32, adding 300 ul of a toluene solution (20 mg/ml) of the ligand B to the zinc oxide ethanol solution, and stirring for half an hour. Then, about 1-1.5 times of the ethyl acetate is added, after it is precipitated and the supernatant is removed by centrifugation, it may be dissolved in 8 mL of the ethanol to obtain a precursor solution.

S33, spin-coating the precursor solution obtained by S32 at a speed of 2000 rpm, placing the substrate in a microwave generator after the spin-coating is completed, and performing a microwave reaction at 70 degrees for 30 minutes, to form an electron transport layer with a porous frame structure.

In one or more embodiments, the porous frame structure of the electron transport layer is formed by the ligand C, and the inorganic oxide nanoparticles include zinc oxide nanoparticles. The manufacturing method of the electron transport layer includes:

S41, forming zinc oxide nanoparticles.

For example, 0.22 g of zinc acetate is dissolved in 10 mL of DMSO (dimethyl sulfoxide); 0.33 g of tetramethylammonium hydroxide is dissolved in 3.3 mL of ethanol, and then dropped into the zinc acetate solution to react for 20 hours. Precipitation begins after adding about 1 times of ethyl acetate, and continue to add the ethyl acetate until the precipitation does not increase after adding about 1.5 times of the ethyl acetate. Centrifuge at 4200 rpm for 5 minutes at 20 degrees Celsius. Then the supernatant is poured off, 10 ml of the ethanol is added, and a zinc oxide ethanol solution is formed by dissolving via ultrasonication for 30 s or shaking for 30 s.

S42, adding 300 ul of a toluene solution (20 mg/ml) of the ligand C to the zinc oxide ethanol solution, and stirring for half an hour. Then, about 1-1.5 times of the ethyl acetate is added, after it is precipitated and the supernatant is removed by centrifugation, it may be dissolved in 8 mL of the ethanol to obtain a precursor solution.

S43, spin-coating the precursor solution obtained by S42 at a speed of 2000 rpm, placing the substrate in a microwave generator after the spin-coating is completed, and performing a microwave reaction at 120 degrees for 60 minutes, to form an electron transport layer with a porous frame structure.

Reference herein to "one embodiment," "an embodiment," or "one or more embodiments" means that a particular feature, structure, or characteristic described in connection with an embodiment is included in at least one embodiment of the present disclosure. Also, please note that instances of the phrase "in one embodiment" herein are not necessarily all referring to the same embodiment.

In the specification provided herein, numerous specific details are set forth. It will be understood, however, that the embodiments of the present disclosure may be practiced without these specific details. In some instances, well-known methods, structures, and techniques have not been shown in detail in order not to obscure an understanding of this specification.

Finally, it should be noted that the above embodiments are only used to illustrate the technical solutions of the present disclosure, but not to limit them; although the present disclosure has been described in detail with reference to the foregoing embodiments, those of ordinary skill in the art should understand that: they may still modify the technical solutions recorded in the foregoing embodiments, or they may equivalently replace some technical features thereof; and these modifications or replacements do not make the essence of the corresponding technical solutions deviate from the spirit and scope of the technical solutions of the embodiments of the present disclosure.

The invention claimed is:

1. A luminescent device, wherein the luminescent device comprises: an anode, a quantum dot light-emitting layer, an electron transport layer, and a cathode in a stacked arrangement;
   the electron transport layer comprises inorganic oxide nanoparticles and a porous frame structure, and the inorganic oxide nanoparticles are anchored in pores of the porous frame structure;
   the porous frame structure is configured to be formed by a ligand reaction; a general structural formula of the ligand comprises: A-X-Q;
   wherein, A is a coordinating group, and is configured to coordinate with the inorganic oxide nanoparticles, X is a regulator group, and is configured to increase or decrease an electron mobility, and Q is a frame group, and is configured to form a frame structure.

2. The luminescent device according to claim 1, wherein A comprises any one of an amino,

3. The luminescent device according to claim 1, wherein X comprises any one of a triphenylamine unit, a carbazole unit, and a pyridine unit.

4. The luminescent device according to claim 1, wherein Q comprises any one of a first group unit, a hydroxyl group, and a cyanide group; wherein the first group unit comprises a first group and a second group, the first group comprises a boronic acid group, and the second group comprises halogen.

5. The luminescent device according to claim 1, wherein the ligand comprises any one

6. The luminescent device according to claim 5, wherein when the ligand comprises the porous frame structure comprises wherein R represents

7. The luminescent device according to claim 5, wherein when the ligand comprises the porous frame structure comprises

8. The luminescent device according to claim 5, wherein when the ligand comprises the porous frame structure comprises 9. The luminescent device according to claim 1, wherein the inorganic oxide nanoparticles comprise any one of zinc oxide nanoparticles, zirconia nanoparticles, aluminum oxide nanoparticles, magnesium zinc oxide nanoparticles, magnesium oxide nanoparticles, and titanium dioxide nanoparticles.

10. The luminescent device according to claim 1, wherein the luminescent device is inverted, and a material of the cathode comprises indium tin oxide.

11. A display apparatus, wherein the display apparatus comprises: a plurality of luminescent devices wherein, each of the luminescent devices comprises: an anode, a quantum dot light-emitting layer, an electron transport layer, and a cathode in a stacked arrangement;
the electron transport layer comprises inorganic oxide nanoparticles and a porous frame structure, and the inorganic oxide nanoparticles are anchored in pores of the porous frame structure;
the porous frame structure is configured to be formed by a ligand reaction: a general structural formula of the ligand comprises: A-X-Q;
wherein, A is a coordinating group, and is configured to coordinate with the inorganic oxide nanoparticles, X is a regulator group, and is configured to increase or decrease an electron mobility, and Q is a frame group, and is configured to form a frame structure.

12. A manufacturing method of the luminescent device according to claim 1, wherein the method comprises:
forming the anode, the quantum dot light-emitting layer, the electron transport layer, and the cathode in the stacked arrangement on a substrate; wherein the electron transport layer comprises the inorganic oxide nanoparticles and the porous frame structure, the inorganic oxide nanoparticles are anchored in the pores of the porous frame structure; the porous frame structure is configured to be formed by reacting with the ligand; the general structural formula of the ligand comprises: A-X-Q; A is the coordinating group, and is configured to coordinate with the inorganic oxide nanoparticles, X is the regulator group, and is configured to increase or decrease the electron mobility, and Q is the frame group, and is configured to form the frame structure.

13. The manufacturing method according to claim 12, wherein forming the electron transport layer comprises:

forming an inorganic-oxide-nanoparticle material and a ligand material, respectively;

mixing the inorganic-oxide-nanoparticle material and the ligand material, to form a precursor material;

coating the precursor material on the substrate; and performing a microwave reaction to the substrate formed with the precursor material, to obtain the electron transport layer.

14. The manufacturing method according to claim 13, wherein performing the microwave reaction to the substrate formed with the precursor material comprises:

placing the substrate formed with the precursor material in a microwave generator, and performing the microwave reaction at a preset temperature for a preset time.

15. The manufacturing method according to claim 14, wherein a range of the preset temperature is 50° C.-200° C., and the preset time is 5 minutes to 60 minutes.

16. The manufacturing method according to claim 12, wherein forming the anode, the quantum dot light-emitting layer, the electron transport layer, and the cathode in the stacked arrangement on the substrate comprises:

sequentially forming the cathode, the electron transport layer, the quantum dot light-emitting layer, and the anode in the stacked arrangement.

17. The display apparatus according to claim 11, wherein A comprises any one of an amino, 18. The display apparatus according to claim 11, wherein X comprises any one of a triphenylamine unit, a carbazole unit, and a pyridine unit.

19. The display apparatus according to claim 11, wherein Q comprises any one of a first group unit, a hydroxyl group, and a cyanide group; wherein the first group unit comprises a first group and a second group, the first group comprises a boronic acid group, and the second group comprises halogen.

20. The display apparatus according to claim 11, wherein the ligand comprises any one of: